US00PP19776P2

(12) United States Plant Patent
Carruth

(10) Patent No.: US PP19,776 P2
(45) Date of Patent: Feb. 24, 2009

(54) CLIMBING ROSE PLANT NAMED 'WEKROSOPELA'

(50) Latin Name: *Rosa hybrida*
Varietal Denomination: WEKrosopela

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 11/985,891

(22) Filed: Nov. 19, 2007

(51) Int. Cl.
*A01H 5/00* (2006.01)

(52) U.S. Cl. ..... Plt./114

(58) Field of Classification Search ..... Plt./114
See application file for complete search history.

(56) References Cited

PUBLICATIONS http://web.archive.org/web/20061028175247/http://www.edmundsroses.com/cgi–bin/browse.cgi?page=item&cat=12&item=352.*
"Edmunds'Roses", 2007 AARS Winners! Catalog, edmundsrose.com 2 pages.

* cited by examiner

*Primary Examiner*—Annette H Para
*Assistant Examiner*—S. B McCormick Ewoldt
(74) *Attorney, Agent, or Firm*—McKee, Voorhees & Sease, P.L.C.

(57) ABSTRACT

A new variety of Climbing rose suitable for garden decoration, having flowers of rosy pink striped with ivory yellow coloration.

1 Drawing Sheet

Classification:
The present invention relates to a new *Rosa hybrida* plant.
Variety denomination:
The new plant has the varietal denomination 'WEKrosopela'.

BACKGROUND OF THE INVENTION

This invention relates to a new and distinct variety of Climbing Rose. It has as its seed parent the variety known as 'WEKtorroc' not patented) and as its pollen parent the variety known as 'SCRivo' (not patented).

SUMMARY OF THE INVENTION

Among the features which distinguish the new variety from other presently available and commercial rose cultivars known to the inventor are the following combinations of characteristics: its unique flowers of rosy pink striped with ivory yellow coloration, its red suffusion on the rachis, its very good repeat flowering and its large and abundant dark blue-green foliage. The plant has a spreading climbing growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKrosopela' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKtorroc' by the following combination of characteristics: whereas 'WEKrosopela' bears semi-double flowers (about 9 to 18 petals) of rosy pink striped with ivory yellow coloration, 'WEKtorroc' bears double flowers of red and white striped coloration with significantly heavier petalage (about 17 to 25 petals). The new variety bears large and abundant dark blue-green foliage, whereas the seed parent bears significantly smaller and less abundant olive green foliage.

The new variety may be distinguished from its pollen parent, 'SCRivo' by the following combination of characteristics: whereas 'WEKrosopela' bears semi-double flowers (about 9 to 18 petals) of rosy pink striped with ivory yellow coloration, 'SCRivo' bears double flowers of creamy white coloration with significantly heavier petalage (about 20 to 24 petals). The new variety is classified as a climbing rose with a spreading climbing growing habit, whereas the pollen parent is classified as a floribunda rose with a significantly shorter and more compact growing habit.

COMPARISON WITH THE CLOSEST COMMERCIALLY AVAILABLE CULTIVAR

The closest commercially available cultivar to the new variety is the seed parent 'WEKtorroc'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. the month of November. Phenotypic expression may vary with environmental, cultural and climatic conditions, as well as differences in conditions of light and soil.

BOTANICAL DESIGNATION:

The new variety botanical designation is *Rosa hybrida* 'WEKrosopela'.

Flower:

The new variety sometimes bears its flowers singly, usually in clusters of two to seven or more per stem. Flowers may be borne in regular rounded clusters on irregular length stems (about 18 to about 100 cm.). Outdoors, the plant blooms abundantly and nearly continuously during the growing season. The flowers have a slight tea fragrance.

Bud:

The peduncle is about 2.2 to about 5.9 cm. in length, of average caliper (about 0.2 to about 0.3 cm. in diameter), and usually erect to moderately stiff. It is moderately smooth, with some stipitate glands. Peduncle color is between 146C and 138B sometimes lightly suffused with near 187B.

Before the calyx breaks, the bud is about 1.2 to about 1.6 cm. in diameter at the widest point, about 1.6 to about 2.0 cm. in length, and pointed to somewhat ovoid in shape with a somewhat conspicuous neck. The surface of the bud bears few foliaceous appendages and very few stipitate glands, usually with slender entire foliaceous parts extending beyond the tip of the bud about ½ or more of its length. Bud color is between 146A and 138B sometimes lightly suffused with near 187B.

The sepals are about 2.5 to about 3.2 cm. in length and about 0.7 to about 1.0 cm. in width at the widest point. The outer surface color of the sepal is between 146A and 138B sometimes lightly suffused with near 187B. The inner surface color of the sepal is between 137A and 146C and covered with fine wooly tomentum; sepal margins are lined with few stipitate glands and some hairs.

The receptacle of the flower is of moderately long length (about 0.7 to about 1.1 cm.) and somewhat heavy in caliper (about 0.7 to about 0.9 cm. in diameter). The receptacle is somewhat cup-shaped, flat at the top and rounded at its base. Its surface is very smooth with thick fleshy walls. The receptacle color is between 144A and 138B.

As the petals open (after the calyx breaks), the bud is about 1.6 to about 2.6 cm. in diameter at the widest point, about 2.3 to about 3.3 cm. in length, and pointed to somewhat ovoid in form. The color of the under surfaces of the newly opened petals is irregularly striped and flecked with as dark as between 53C and 57C to as light as between 11B and 11C. At the point where the petal attaches, there is a somewhat large zone of between 8B and 9C. The color of the upper surfaces of the newly opened petals is irregularly striped and flecked with as dark as between 53B and 57C to as light as between 14D and 11C. At the point where the petal attaches, there is a moderately large zone of between 9A and 7A Bloom:

When fully open, the bloom ranges from about 8.5 to about 11.1 cm. in diameter. Petalage is semi-double with about 9 to 18 petals and about 3 to 5 petaloids irregularly arranged. When partially open, the bloom form is moderately flat at the top to somewhat cupped, and the petals are moderately tightly spiraled to cupped with petal edges somewhat reflexed outward. When fully open, the bloom form is cupped, and the petals are loosely cupped with petal edges moderately reflexed outward.

Petals:

The substance of the petals is somewhat heavy and of medium thickness, with upper surfaces moderately satiny and under surfaces shiny. The petals are about 4.9 to about 6.0 cm. in length and about 4.8 to about 6.4 cm. in width at the widest point. Petal margins are entire.

The outer petals are rounded in shape with rounded apices.

The inner petals are nearly round to somewhat obovate in shape with rounded apices.

Petaloids are about 2.0 to about 5.1 cm. in length and about 1.3 to about 5.2 cm. in width at the widest point. Petaloids are irregularly shaped moderately obovate to somewhat oblanceolate with rounded apices.

Newly opened flower:

The under surface color of the outer petals is irregularly striped and flecked with as dark as between 63B and 64C to as light as between 8D and 155D. At the point where the petal attaches, there is a somewhat large zone of between 6C and 10B. The upper surface color of the outer petals is irregularly striped and flecked with as dark as between 67A and 57C to as light as between 10D and 155D. At the point where the petal attaches, there is a moderately large zone of between 9B and 7B.

The under surface color of the intermediate and inner petals is irregularly striped and flecked with as dark as between 63A and 57C to as light as between 8D and 155D. The upper surface color of the intermediate and inner petals is irregularly striped and flecked with as dark as between 66A and 57C to as light as between 10D and 155D.

The under and upper surface color of the petaloids are similar in coloration to the upper and under surfaces of the intermediate and inner petals.

The general tonality of the newly opened flower is irregularly striped and flecked with as dark as between 66A and 57C to as light as between 10D and 155D.

Three-day-old flower:

The under surface color of the outer, intermediate and inner petals is irregularly striped and flecked with as dark as between 67D and 67C to as light as between 155A and 155D. At the point where the petal attaches, there is a somewhat large zone of near 4D. The upper surface color of the outer, intermediate and inner petals is irregularly striped and flecked with as dark as between 67B and 67C to as light as between 155A and 155D. At the point where the petal attaches, there is a moderately large zone of between 8B and 10C.

The under and upper surface color of the petaloids are similar in coloration to the upper and under surfaces of the intermediate and inner petals.

The general tonality of the three-day-old flower is irregularly striped and flecked with as dark as between 67B and 67C to as light as between 155A and 155D.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

Male reproductive organs:

Stamens are many in number (average about 140) and are arranged regularly about the pistils; a few are mixed with petaloids. The filaments are of long length (about 0.6 to about 1.5 cm.) most with anthers. Filaments are between 9A and 12A in color. The anthers are somewhat small for the class and all open approximately at the same time. Anther color when immature is near 22A on the external part and near 11B on the internal part. Anther color at maturity is near 165B on the external part and near 200A on the internal part. Pollen is very abundant and near 15B in color.

Female reproductive organs:

Pistils vary in number (average about 100). The styles are somewhat uneven, average to somewhat short in length (about 0.3 to about 0.5 cm.), thin in caliper and moderately separated. Stigma color is between 2C and 3C. Style color is between 154D and 149D. Ovaries are usually all enclosed in the calyx.

Hips are of average length (about 1.5 to about 2.4 cm.), rounded to somewhat globular in form, and between 42A and 34A in color when ripe. The hip surface is very smooth with thick fleshy walls. The sepals are somewhat fugacious, and usually straight in shape.

The seeds are irregularly rounded, smooth in texture, approximately 8 to about 14 per hip, about 0.3 to about 0.6 cm. in diameter at the widest point and between 164C and 161B in color.

Foliage:

The compound leaves are usually comprised of three to seven leaflets and are borne abundantly. The seven-leaflet leaves are about 9.8 to about 13.1 cm. in length and about 7.1 to about 11.3 cm. in width at the widest point, moderately heavy to somewhat leathery in texture, and glossy in finish on the upper surface and matte on the under surface. The terminal leaflets are about 4.8 to about 7.0 cm. in length and about 3.5 to about 5.5 cm. in width at the widest point, shaped moderately ovate to somewhat oval with acuminate apices and rounded to somewhat acute bases. Their margins are usually simply serrate.

The upper surface color of the mature leaf is between 139A and 137B. The under surface color of the mature leaf is between 137C and 146B. The upper surface color of the young leaf is between 137B and 146B, sometimes lightly suffused especially on the edge with between 187A and 187B. The under surface color of the young leaf is between 146B and 144A, sometimes lightly suffused with between 187B and 187C.

The rachis is moderately heavy in caliper and somewhat rough. The upper side is deeply grooved with few hairs and some stipitate glands on the edges of the grooves. The under side of the rachis is somewhat rough with very few stipitate glands and few small prickles. The rachis color is near 146D on the under side and near 137B on the upper side sometimes lightly suffused with between 187A and 187B.

The stipules are about 1.0 to about 1.7 cm. in length and of medium width (about 0.4 to about 0.7 cm.) with medium length straight points that sometime turn out at an angle of more than 45 degrees and sometimes recurve toward the stem. The stipule color is between 137B and 146B sometimes lightly suffused with between 187C and 187D.

The petiole is moderately heavy in caliper and somewhat rough. The upper side is deeply grooved with few hairs and some stipitate glands on the edges of the grooves. The under side of the petiole is somewhat rough with very few stipitate glands and few small prickles. The petiole is about 0.3 to about 0.7 cm. in length and about 0.1 to about 0.2 cm in diameter at the widest point. The petiole color is near 146D on the under side and near 137B on the upper side sometimes lightly suffused with between 187A and 187B.

The plant displays an above average degree of resistance to powdery mildew and rust as compared to other commercial varieties grown under comparable conditions in Pomona, Calif. The plant's winter hardiness and drought/heat tolerance are yet to be determined.

Growth:

The plant has a spreading climbing growing habit with canes about 250 to about 380 cm. in length with full branching. It displays very vigorous growth and the canes are of somewhat heavy caliper for the class.

The color of the major stems is between 148A and 152A. The major stems are about 1.80 to about 3.10 cm. in diameter at their widest point. They bear several large prickles that are about 0.7 to about 1.0 cm. in length. The large prickles are angled moderately downward with a moderately short somewhat broad oval base; prickle color is between 165B and 164A. The major stem bears some small prickles of similar shape and coloration.

The color of the branches is between 146B and 146A. They bear some large prickles which are of similar size and shape to the large prickles on the major stems; prickle color is between 164C and 161A sometimes lightly suffused with between 187C and 183C. The branches bear some small prickles of similar shape and coloration.

The color of the new shoots is between 146C and 138B sometimes lightly suffused with between 187B and 183B. They bear some large prickles which are of similar size and shape to the large prickles on the major stems; prickle color is between 153A and 160A often moderately suffused with between 187C and 187D. The shoots bear some small prickles of similar shape and coloration.

I claim:

1. A new and distinct Climbing rose plant of the variety substantially as described and illustrated herein.

* * * * *

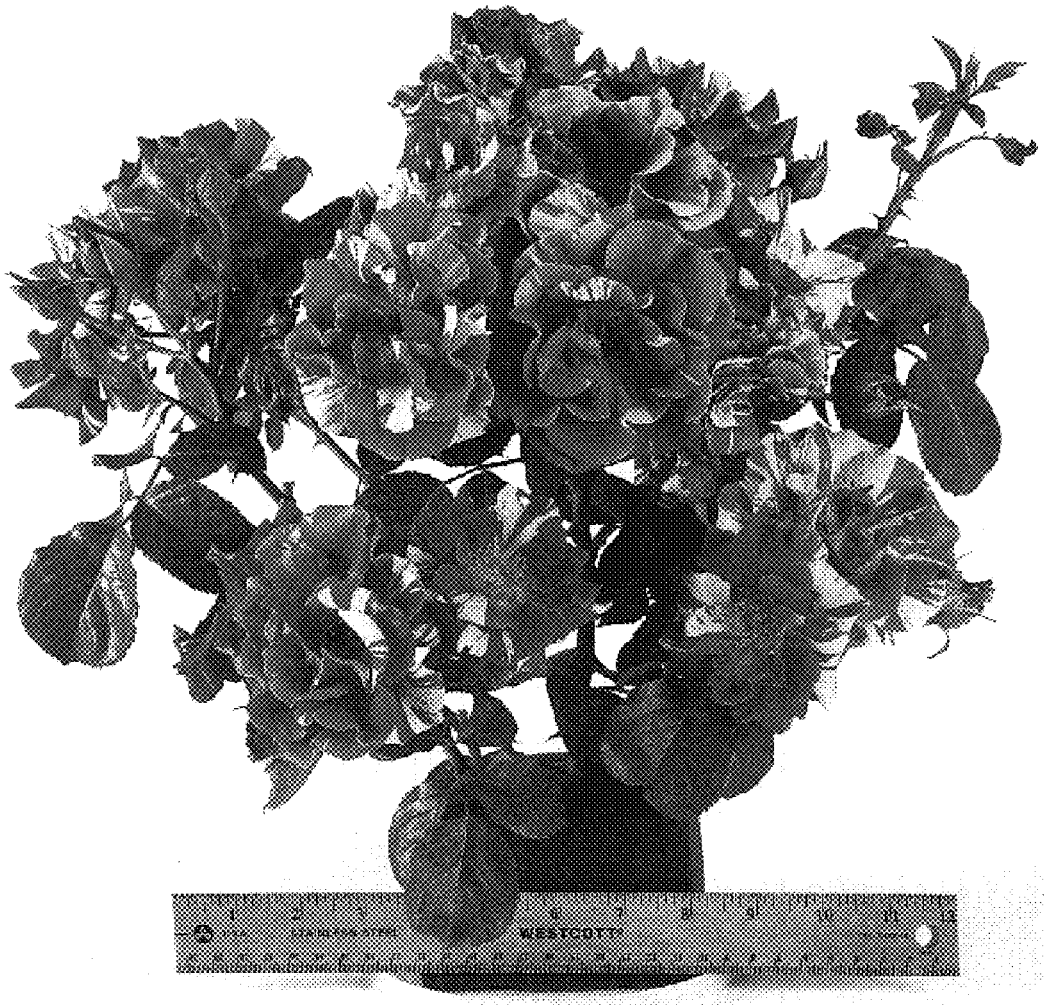
WESTCOTT